United States Patent
Farling et al.

(10) Patent No.: US 7,175,630 B2
(45) Date of Patent: Feb. 13, 2007

(54) BONE CUTTING TEMPLATE AND METHOD OF USE

(75) Inventors: Toby N. Farling, Warsaw, IN (US); Warren Scott Gareiss, Columbia City, IN (US); Robert A. Hodorek, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 514 days.

(21) Appl. No.: 10/357,279

(22) Filed: Feb. 3, 2003

(65) Prior Publication Data

US 2004/0153085 A1   Aug. 5, 2004

(51) Int. Cl.
*A61F 5/00* (2006.01)
(52) U.S. Cl. ...................................................... 606/87
(58) Field of Classification Search ................. 606/53, 606/86, 87, 88, 89, 102
See application file for complete search history.

(56) References Cited

U.S. PATENT DOCUMENTS

| | | | |
|---|---|---|---|
| 5,364,401 A * | 11/1994 | Ferrante et al. ............... | 606/84 |
| 5,514,139 A | 5/1996 | Goldstein et al. | |
| 5,540,696 A * | 7/1996 | Booth et al. .................. | 606/88 |
| 5,562,675 A * | 10/1996 | McNulty et al. ............... | 606/96 |
| 5,597,379 A | 1/1997 | Haines et al. | |
| 5,643,272 A | 7/1997 | Haines et al. | |
| 5,688,280 A * | 11/1997 | Booth et al. .................. | 606/88 |
| 5,755,803 A | 5/1998 | Haines et al. | |
| 5,810,827 A | 9/1998 | Haines et al. | |
| 5,879,354 A | 3/1999 | Haines et al. | |
| 5,916,220 A * | 6/1999 | Masini ........................ | 606/88 |
| 6,056,754 A | 5/2000 | Haines et al. | |
| 6,106,529 A * | 8/2000 | Techiera ...................... | 606/88 |
| 6,197,064 B1 | 3/2001 | Haines et al. | |
| 6,290,704 B1 * | 9/2001 | Burkinshaw et al. ......... | 606/88 |
| 6,695,848 B2 | 2/2004 | Haines et al. | |

* cited by examiner

*Primary Examiner*—Eduardo C. Robert
*Assistant Examiner*—Anu Ramana
(74) *Attorney, Agent, or Firm*—Baker & Daniels LLP

(57) ABSTRACT

The present invention comprises a set of instruments and a method for their use in preparing a knee joint to receive knee implants. The inventive instruments and method are generally suitable for knee joint surgery. Furthermore, they include features that make them suitable for performing a minimally invasive knee surgery in which a smaller than normal incision is made and oriented. An illustrative set of instruments including an A/P sizer and femoral finishing guide for total knee arthroplasty and an associated minimally invasive technique are described.

18 Claims, 3 Drawing Sheets

BONE CUTTING TEMPLATE AND METHOD OF USE

FIELD OF THE INVENTION

The present invention relates to methods and instruments for performing bone surgery.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DESCRIPTION OF THE ILLUSTRATED EMBODIMENTS

The present invention relates to methods and instruments for performing bone surgery. For example, in knee arthroplasty, an incision is made into the knee joint to expose the bones comprising the joint. Cutting guides are then used to guide the removal of the articular surfaces that are to be replaced. In particular, a femoral finishing guide is used to guide a cutter to make the final cuts to prepare the femur to receive a prosthetic implant. The present instruments and method are generally suitable for knee joint surgery. Furthermore, they include features that make them suitable for performing a minimally invasive knee surgery in which a smaller than normal incision is made and oriented to least disturb the soft tissues supporting the knee joint.

Figure 1:
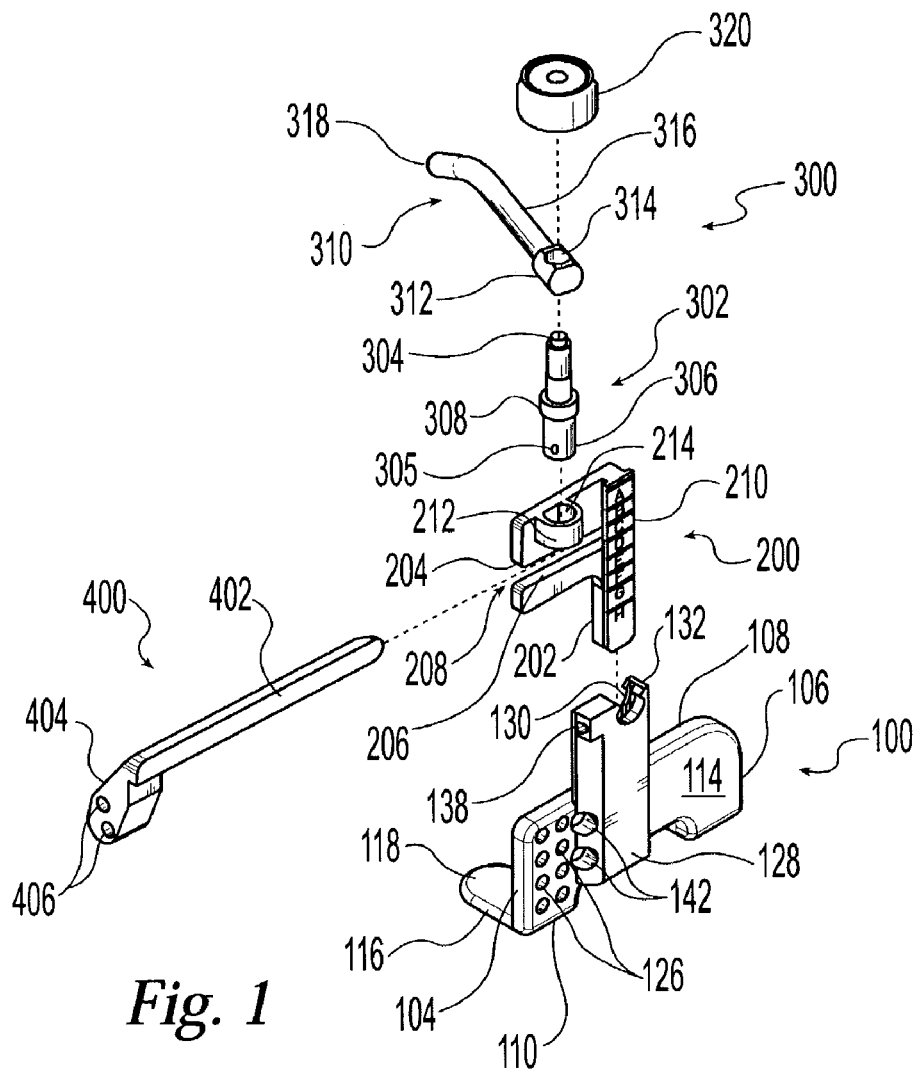
FIG. 1 is an exploded perspective view of an illustrative femoral anterior/posterior sizer according to the present invention.
Figure 2:
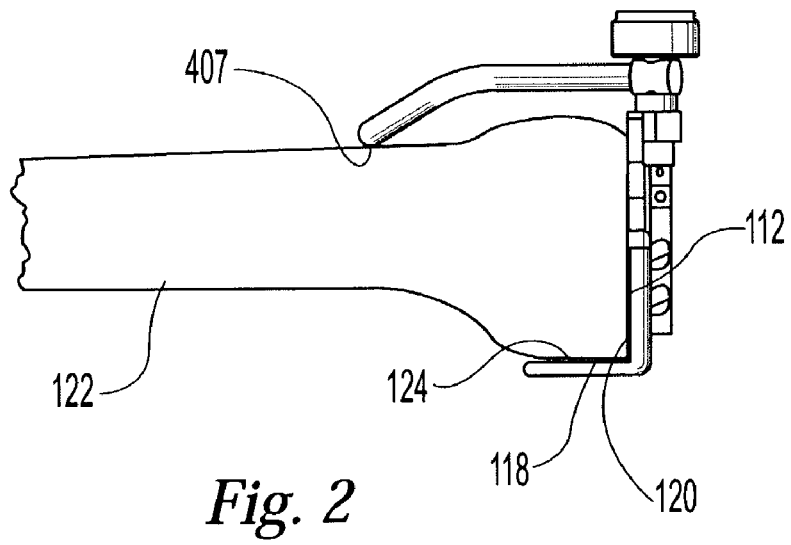
FIG. 2 is a side elevation view of the sizer of FIG. 1 mounted on a bone.
Figure 3:
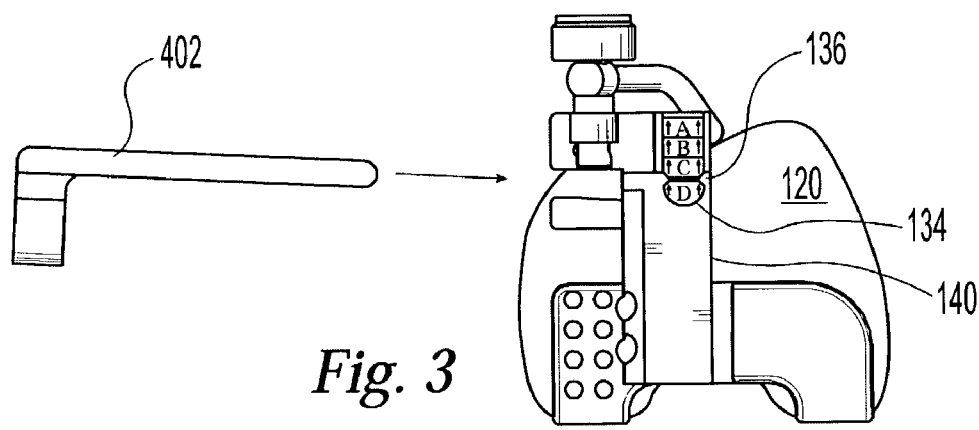
FIG. 3 is a front elevation view of the sizer of FIG. 1 mounted on a bone.

An illustrative set of instruments for bone surgery will be described with reference to the drawings. FIGS. 1–3 depict an anterior/posterior (AP) sizer for knee arthroplasty. This particular example is adapted for a minimally invasive side approach to the knee joint in which the distal femur has been cut to form a flat distal surface 120 and will be described from a left medial perspective. The A/P sizer comprises a base 100, a slide 200, a boom assembly 300, and a reference rail 400. The base 100 includes a flat, plate-like body having a proximal face 112, a distal face 114 and medial 104, lateral 106, anterior 108, and posterior 110 sides. The proximal face 112 forms a distal reference surface for indexing against the cut distal surface 120 of a femur 122. A pair of feet 116 is attached to the base adjacent the posterior side and projects proximally. The feet 116 include posterior reference surfaces 118 perpendicular to the distal reference surface and facing anteriorly to index against the posterior femoral condyles 124.

The base 100 includes a plurality of fixation holes 126 extending from the proximal face 112 to the distal face 114 adjacent the medial side 104 of the base 100. The exemplary fixation holes 126 are sized to receive a ⅛ inch fixation pin to hold the base 100 in place against the cut distal femur 120. A riser 128 is formed on the distal face of the base 100 and extends anteriorly beyond the anterior side 108 of the base 100. The riser includes a slide receiving channel 130 extending from the anterior end 132 of the riser posteriorly. In the exemplary embodiment, the channel 130 has a dovetail cross section to prevent rotation or proximal-distal translation of like-shaped members inserted into the passageway, while allowing anterior-posterior translation. A cut out window 134 adjacent the anterior end 132 of the riser permits viewing into the channel 130. Pointer 136 formed on the side of the window 134 provides a convenient reference point. A ball detent 138 is mounted in a bore in communication with the channel 130 adjacent the anterior end 132 of the riser. The riser 128 is offset medially so that the lateral edge 140 of the riser is aligned with the center of the base 100. A pair of threaded handle receiving openings 142 are formed in the riser at an angle facing medially and distally.

The slide 200 comprises a generally L-shaped body having a sliding portion 202, a first reference extension 204, and a second reference extension 206. The first and second reference extensions are parallel to one another and angled relative to the sliding portion to form a reference channel 208 between them angled relative to the sliding portion. The sliding portion 202 has a dovetail cross section and includes size indicia 210 formed on a distal face. A collar 212 having a bore 214 is mounted adjacent the anterior end of the slide 200.

The sliding portion 202 is received in the slide receiving channel 130 of the base 100 for anterior-posterior translation. The reference channel 208 angles downwardly from medial to lateral at an angle of approximately 3° relative to the posterior reference surfaces 118. The ball detent 138 is biased against the side of the sliding portion 202 to create a frictional force that helps to maintain the slide in a user selected position while permitting easy readjustment. The indicia 210 are viewable through the window 134 relative to the pointer 136.

The boom assembly 300 comprises a boom base 302, a boom 310, and a boom retaining nut 320. The boom base 302 comprises a shaft having a boom receiving end 304, a mounting end 306, and a raised annular portion 308 between the two ends. The mounting end 306 includes a ball detent 305 biased radially outwardly. The boom 310 comprises a collar 312 having a cylindrical through bore 314 and an arm 316 extending from the collar to a tip 318. The tip 318 is located radially outwardly and downwardly relative to the collar. The boom 310 is received on the boom base 302 with the receiving end 304 engaging the bore 314 and the collar 312 abutting the annular portion 308. The boom retaining nut 320 threads onto receiving end 304 to hold the assembly together. The boom assembly 300 is received on the slide 200 with the mounting end 306 engaging the slide collar bore 214 and the annular portion 308 abutting the slide collar 212. As the annular portion 308 abuts the slide collar 212, the ball detent 305 extends below the slide collar and in contact with the lower edge of the slide collar 212 to bias the boom assembly 300 downwardly and releasably lock it in place. Thus assembled the boom tip 318 is a predetermined fixed distance from the reference channel 208. The distance between the boom tip 318 and the posterior reference surface 118 is indicated by the particular one of the slide indicia 210 that is aligned with the pointer 136 in the base window 134. Likewise, with a particular one of the indicia 210 aligned with the pointer 136, the reference extensions 204, 206 and the channel 208 are located at a corresponding known distance from the posterior reference surface 118.

The reference rail 400 comprises a generally L-shaped body having a guide rail 402 and a rail mounting base 404. The guide rail 402 comprises an elongate bar of rectangular cross section. Alternatively, the bar could be round, dovetail shaped, or of other suitable shape. The rail mounting base 404 includes fixation holes 406 extending through it for receiving fixation pins to hold the rail 400 on a bone. The guide rail 402 is receivable in close fitting, sliding relationship within the reference channel 208 of the slide 200.

Figure 4:
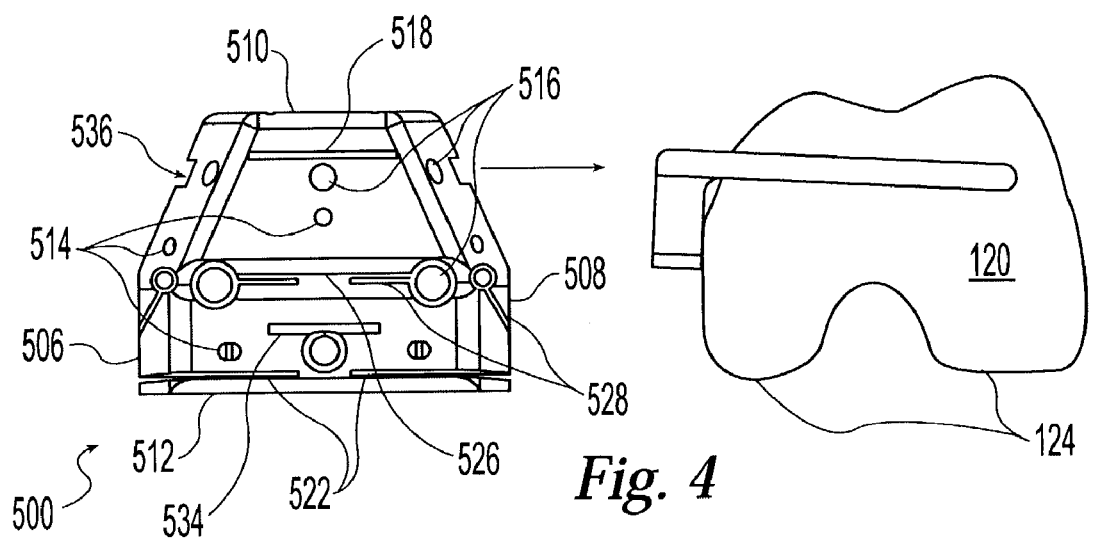
FIG. 4 is a front elevation view of an illustrative femoral finishing guide according to the present invention being mounted on a bone.
Figure 5:
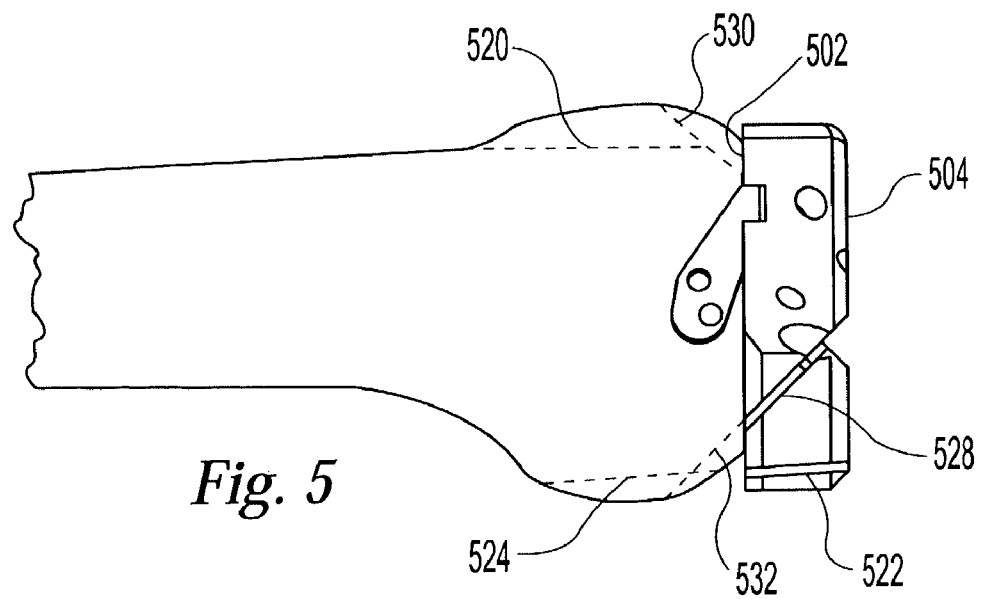
FIG. 5 is a side elevation view of the finishing guide of FIG. 4 mounted on a bone.

FIGS. 4–5 depict an illustrative cut block in the form of a femoral finishing guide 500. The femoral finishing guide 500 comprises a slab-like body having a proximal face 502, a distal face 504, and medial 506, lateral 508, anterior 510, and posterior 512 sides. The proximal face 502 forms a distal reference surface for indexing against the cut distal surface 120 of a femur 122. The guide 500 includes a variety of small 514 and large 516 fixation holes to receive fasteners to secure the guide 500 to the cut distal surface 120. Fasteners include a variety of designs as known in the art such as pins and screws. The guide 500 further includes cutter guides to guide a cutter to make femoral box cuts to prepare the femur to receive a femoral implant. In the illustrative embodiment, the cutter guides comprise saw blade slots for guiding a saw blade. An anterior cut slot 518 guides a saw blade generally proximal-distally to form a flat surface 520 on the anterior femur. Posterior cut slots 522 guide a saw blade generally proximal-distally to form flat surfaces 524 on the poster aspects of the femoral condyles. Anterior 526 and posterior 528 chamfer cut slots guide a saw blade to form anterior 530 and posterior 532 chambers between the distal cut surface 120 and the anterior 520 and posterior 524 surfaces respectively. A trochlear cut slot 534 guides a saw blade to form a trochlear recess. The proximal face 502 of the cut guide includes a rail receiving channel 536 having a cross sectional shape to allow it to receive the guide rail 402 in close fitting, sliding relationship.

The A/P sizer is used to determine the size of the distal femur for implant selection purposes and to create a datum on the distal femur to be used to orient subsequent bone cuts made with the femoral finishing guide. In use, the sizer base 100 is positioned with the distal reference surface 112 against the cut distal femur 120. The base is slid anteriorly until the posterior reference surfaces 118 contact the posterior condyles 124 to align the base with the plane containing the posterior most aspects of the posterior condyles 124 and perpendicular to the distal cut surface 120. To facilitate gripping and positioning the base, a handle can be screwed into one of the handle openings 142. Fasteners can be placed through the fixation holes 126 to hold the base in position. The two handle openings 142 and plurality of fixation holes 126 allow the handle and fasteners to be positioned for effective use without interfering with one another. Once the base is set, the slide 200, with boom assembly 300 attached, is translated posteriorly until the boom tip 318 touches the appropriate anatomic reference on the anterior cortex 407. The size of the femur, and corresponding implant size, are now read from the slide 200 by viewing through the window 134 in the riser 128 to determine which of the size indicia 210 is adjacent the pointer 136. The reference channel 208 is at a predetermined fixed A/P position relative to the boom tip 318 and thus the anterior femoral cortex 407. Since the reference channel 208 moves with the boom 310 and slide 200, it is positioned at a predetermined A/P position relative to the posterior reference surface 118 corresponding to the indicated size. If the surgeon determines that a size adjustment should be made, e.g. if the size falls between two indicia or for other clinical reasons, he would reposition the boom 310 and slide 200 so that the desired size indicium is aligned with the pointer 136. The reference channel 208 will now overlie the bone at a position corresponding to the adjusted size. However, the boom tip 318 prevents sizing the femur too small, which could position subsequent cuts too far posteriorly and notch the anterior cortex. Once the appropriate size is determined, the guide rail 402 is inserted into the reference channel 208 to position the guide rail at the desired A/P position as determined by the sizing procedure and to set the guide rail 402 at an external rotation angle of 3° relative to the posterior condyles. The guide rail 402 is fixed in place by inserting fasteners through fixation holes 406. Once the guide rail 402 is secured, the rest of the A/P sizer is removed, leaving the guide rail in place on the end of the femur as shown in FIG. 4. The guide rail is now a datum formed on the distal femur that preserves the desired A/P position and external rotation information previously determined and that can be referenced to guide subsequent bone cuts.

The femoral finishing guide 500 is now engaged with the guide rail 402. The rail receiving channel 536 engages the guide rail 402 to orient the guide 500 in the desired A/P position and external rotation and further to allow medial-lateral (M/L) translation of the finishing guide 500 independent of the A/P position and external rotation. The finishing guide 500 is placed in the desired M/L position and secured with fasteners through one or more of the guide fixation holes 514, 516. The guide rail 402 is then removed from the bone leaving the finishing guide 500 in place. Additional fasteners may now be placed in any holes that were obstructed by the guide rail 402 if desired. A saw blade is guided through the saws slots to cut the distal femur to receive an implant.

Figure 6:
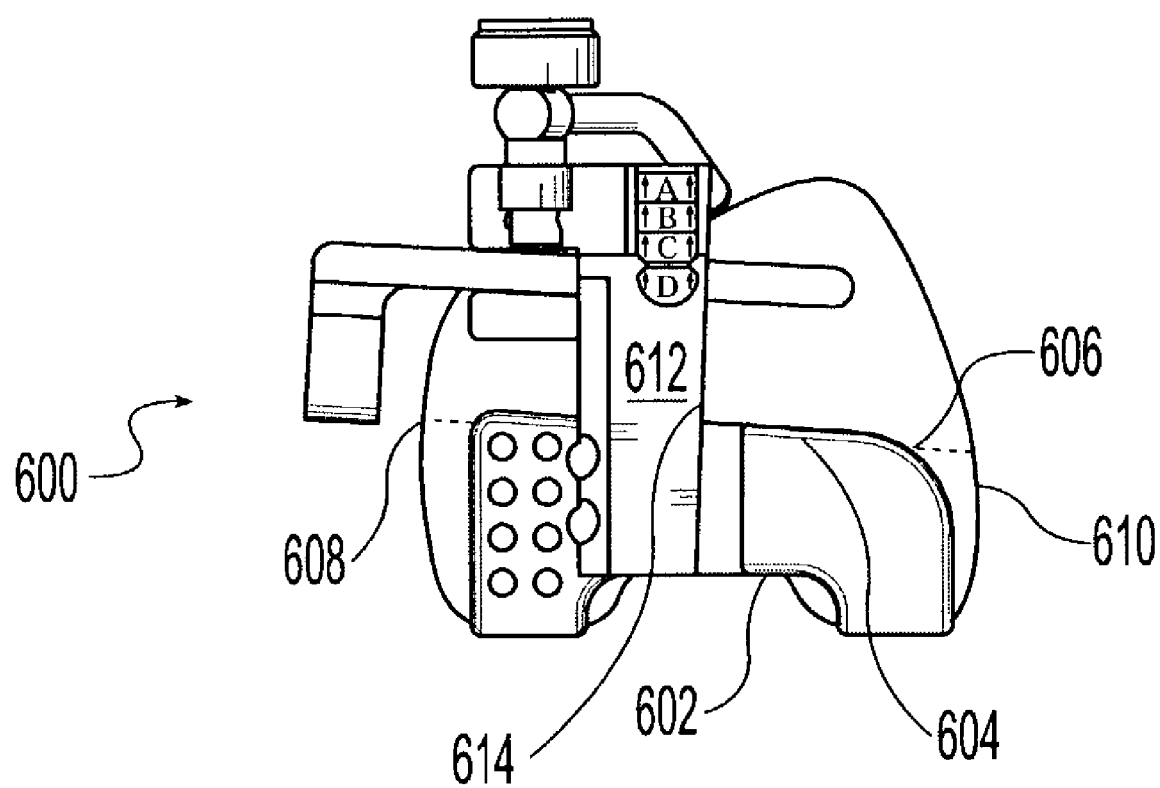
FIG. 6 is a front elevation view of an alternative embodiment of an illustrative femoral anterior/posterior sizer according to the present invention.

As an alternative technique, the external rotation of the guide rail 402 can be established by leaving the A/P sizer loose and rotating it and the guide rail 402 so that the guide rail 402 is parallel to an axis extending through the medial and lateral epicondyles. Likewise, external rotation can be established by orienting the guide rail 402 perpendicular to the A/P axis of the distal femur. The alternative embodiment of an A/P sizer 600 shown in FIG. 6 facilitates these alternative techniques. The A/P sizer 600 is generally similar in layout and function to the A/P sizer of FIGS. 1–3. However, the base 602 includes an anterior side 604 that slopes downwardly from medial to lateral. The angle of the anterior side 604 is approximately the same as the epicondylar axis 606 extending between the medial 608 and lateral 610 femoral epicondyles of the average human femur. This sloping anterior side 604 thus serves as a convenient visual alignment reference for those surgeons who want to orient the guide rail parallel to the epicondylar axis 606. The base 602 also includes a riser 612 having at least one side 614 that is parallel to the A/P axis of the average human femur. The A/P axis is generally perpendicular to the epicondylar axis and so the side 614 of the riser is made perpendicular to the anterior side 604. This angled side 614 thus serves as a convenient visual alignment reference for those surgeons who want to orient the guide rail parallel to the A/P axis.

The exemplary A/P sizer guide and femoral finishing guide embodiments of FIGS. 1–6 include features that are particularly well suited for minimally invasive surgical approaches to knee arthroplasty. These illustrative embodiments are adapted for a left medial minimally invasive surgical approach to a knee. In this approach, a small incision is made on the medial side of the knee. The base 100 is slipped into the incision from medial to lateral, lateral side 106 first. The low proximal-distal profile and medially offset riser facilitate this insertion. Once in place, the lateral side 106 is hidden from view by the overlying soft tissues and is difficult to access. The medial side 104 is more accessible. The medial location and medial-distal orientation of the handle receiving openings 142 allow access through the medial incision to engage and disengage a handle and permit the handle to project through the small, medial incision. Likewise the medial placement of the fixation holes permits access through the incision for the placement of fasteners. The incision is manipulated anteriorly to allow the boom assembly 300 and slide 200 to be engaged with the base and sizing to be performed. The boom base 302 mounting on the slide collar 212 is also offset medially to move bulk away from the tighter aspects of the incision. The relatively slender boom arm 316 and tip 318 reach laterally into the incision to contact the anterior femoral cortex 407. The relatively flat reference rail 400 is inserted from the side to engage the reference channel 208. The femoral finishing guide 500 is compact and tapered to facilitate its being slid in from the side as well. Furthermore, because the femoral finishing guide slides on the reference rail 400 and gets its A%P position and external rotation information from the reference rail 400, it can be accurately positioned even though such a minimally invasive technique calls for an essentially blind placement in which much of the guide will be covered by soft tissues when it is in place. By changing the angle of the reference channel 208 and/or mirroring the A/P sizer geometry, the instrument can be adapted for left/lateral, right/medial, and right/lateral approaches as well. Although specifically adapted to facilitate a side oriented minimally invasive procedure, these instruments are advantageously useable in a traditional centrally oriented open procedure.

It will be understood by those skilled in the art that the foregoing has described illustrative embodiments of the present invention and that variations may be made to these embodiments without departing from the spirit and scope of the invention defined by the appended claims. For example the illustrative embodiments depict using saw guides and blades to make the bone cuts. However, the claimed methods and alignment guides could also be used with other bone removal systems to set their reference bases to achieve the desired position and rotation of prepared bone surfaces.

What is claimed is:

1. A femoral knee instrument combination comprising:
a datum positionable on a femur;
datum placement means for referencing anatomic landmarks to determine a suitable anterior-posterior location and external rotation and means for positioning the datum to record the anterior-posterior location and external rotation information for subsequent reference; and
a femoral cut guide having means for engaging the datum to position the femoral cut guide in the desired anterior-posterior position and external rotation while permitting medial-lateral positioning of the femoral cut guide independent of the anterior-posterior position and external rotation and means for guiding a cutter to cut the distal femur.

2. The combination of claim 1 wherein the datum comprises a rail extending approximately medial-laterally across the distal end of the femur.

3. The combination of claim 1 wherein the means for referencing anatomic landmarks comprises a rotation reference alignable with at least one of the posterior femoral condyles, anterior-posterior distal femoral axis, and epicondylar axis.

4. The combination of claim 3 wherein the rotation reference comprises a surface engageable with at least one posterior femoral condyle, and wherein the combination further comprises a datum guide, a distal reference surface engageable with the distal end of the femur and an anterior reference surface engageable with the anterior femoral cortex, the anterior reference surface being connected to the datum guide and moveable relative to the rotation reference to position the datum guide in known relationship to the reference surfaces.

5. The combination of claim 4 wherein the datum guide comprises a slot and the datum comprises a rail engageable with the slot to position the rail medial-laterally across the distal end of the femur and further wherein the cut guide means for engaging the datum comprises a slot that engages the rail to permit the cut guide to translate medial-laterally on the rail.

6. The combination of claim 5 wherein the means for guiding a cutter guides the cutter to form anterior, anterior chamfer, posterior chamfer, and posterior cuts on the femur.

7. An A/P sizer and femoral finishing guide for preparing the distal end of a femur exposed via an incision, the A/P sizer and femoral finishing guide comprising:
an A/P sizer including a distal reference surface engageable with the distal end of said femur; a posterior reference surface engageable with at least one posterior condyle of said femur; an anterior reference surface engageable with the anterior side of said femur, the anterior reference surface being moveable relative to the posterior reference surface; a datum guide connected to the anterior reference surface so that it moves with the anterior reference surface to a desired position relative to the posterior reference surface; and a datum engageable with the datum guide to position the datum in the desired position relative to the posterior reference surface; and
a femoral cut guide having a datum engaging surface engageable with the datum to position the femoral finishing guide in the desired position and a cutter guide to guide a cutter to cut said femur.

8. The combination of claim 7 wherein the datum guide also forms a predetermined external rotation angle relative to the posterior reference surface so that the datum is placed at the predetermined angle relative to the posterior reference surface.

9. The combination of claim 8 wherein the A/P sizer further comprises a sizer base having a medial side, a lateral side and a centerline between the medial and lateral sides, the sizer base including the distal and posterior reference surfaces and the A/P sizer further comprising a boom having a boom base, a boom tip and a boom arm extending between the base and tip, the boom base being mounted for anterior-posterior translation on the sizer base, the anterior reference surface comprising the tip of the boom.

10. The combination of claim 7 wherein the A/P sizer comprises a base having an alignment edge parallel to the datum guide, the alignment edge being visually alignable with at least one of a parallel epicondylar axis and a perpendicular A/P axis of the distal femur to set the desired external rotation of the datum.

11. The combination of claim 7 wherein the datum comprises a rail, the datum guide of the A/P sizer comprises a channel able to receive the rail, and the datum engaging surface of the femoral finishing guide forms part of a channel that engages the datum.

12. A method for performing knee surgery comprising the steps of:
   positioning a datum on the distal end of the femur at a desired anterior-posterior position and at a desired external rotation angle;
   engaging the datum with a cut guide to constrain the cut guide to medial-lateral translation along the datum on the distal end of the femur;
   translating the cut guide medial-laterally on the datum to a desired medial-lateral position; and
   guiding a cutter with the cut guide to cut the distal end of the femur.

13. The method of claim 12 further comprising the step of making an incision on one of the medial and lateral sides of the knee and wherein the steps are performed through the incision from the side of the knee such that at least one side of the knee joint and surgical instruments placed on the at least one side of the joint are hidden by overlying soft tissues.

14. The method of claim 12 further comprising the step of orienting the datum at a desired external rotation angle by aligning the datum to be parallel to the epicondylar axis of the distal femur.

15. The method of claim 14 further comprising the steps of providing an A/P sizer having a sighting edge, aligning the sighting edge parallel to the epicondylar axis, and then positioning the datum with the A/P sizer.

16. The method of claim 12 further comprising the step of orienting the datum at a desired external rotation angle by aligning the datum to be perpendicular to the distal femoral A/P axis.

17. The method of claim 16 further comprising the steps of providing an A/P sizer having a sighting edge, aligning the sighting edge parallel to the distal femoral A/P axis, and then positioning the datum perpendicular to the sighting edge with the A/P sizer.

18. A method for performing knee surgery comprising the steps of:
   making an incision on one of the medial and lateral sides of the knee to expose the knee joint from the side;
   cutting the distal femur through the incision from the side to form a flat distal cut surface;
   inserting a datum guide through the incision from the side;
   referencing the anterior femoral cortex with the datum guide to establish a desired A/P position;
   orienting the datum guide at a desired external rotation angle;
   positioning a datum on the distal end of the femur through the incision from the side at the desired anterior-posterior position and at the desired external rotation angle;
   engaging the datum with a cut guide through the incision from the side to constrain the cut guide to medial-lateral translation along the datum on the distal end of the femur;
   translating the cut guide medial-laterally on the datum to a desired medial-lateral position; and
   guiding a cutter with the cut guide to cut the distal end of the femur.

* * * * *